(12) United States Patent
Halpern et al.

(10) Patent No.: US 8,588,931 B2
(45) Date of Patent: Nov. 19, 2013

(54) NEURAL STIMULATION

(75) Inventors: Mark Edward Halpern, East Malvern (AU); James Bernard Fallon, Brunswick (AU)

(73) Assignees: National ICT Australia Limited, Eveleigh, NSW (AU); The Bionics Institute of Australia, East Melbourne, Victoria (AU)

( * ) Notice: Subject to any disclaimer, the term of this patent is extended or adjusted under 35 U.S.C. 154(b) by 350 days.

(21) Appl. No.: 12/885,174

(22) Filed: Sep. 17, 2010

(65) Prior Publication Data

US 2011/0071600 A1    Mar. 24, 2011

Related U.S. Application Data

(60) Provisional application No. 61/243,693, filed on Sep. 18, 2009.

(51) Int. Cl.
*A61N 1/18* (2006.01)

(52) U.S. Cl.
USPC ............. 607/72; 607/2; 607/68; 607/74

(58) Field of Classification Search
USPC .................. 607/2, 39–58, 63, 68–72, 74
See application file for complete search history.

(56) References Cited

U.S. PATENT DOCUMENTS

| | | | |
|---|---|---|---|
| 4,690,145 A | 9/1987 | King-Smith et al. | |
| 4,754,759 A | 7/1988 | Allocca | |
| 7,801,600 B1 * | 9/2010 | Carbunaru et al. | 607/2 |
| 2003/0163166 A1 * | 8/2003 | Sweeney et al. | 607/5 |
| 2006/0167512 A1 * | 7/2006 | Ross et al. | 607/11 |

FOREIGN PATENT DOCUMENTS

| | | |
|---|---|---|
| EP | 1 224 950 | 7/2002 |
| WO | WO 00/00251 | 1/2000 |

OTHER PUBLICATIONS

Mark Halpern et al., "Current Waveforms for Neural Stimulation Charge Delivery with Reduced Maximum Electrode Voltage", IEEE, 2010., 8 pages.

Mark Halpern, "Optimal Design of Neural Stimulation Current Waveforms", 31st Annual International Conference of the IEEE EMBS, Minnesota, USA, Sep. 2-6, 2009, pp. 189-192.

Douglas Philip Dean, "Modelling Neural Transduction", B.A.SC., Engineering Physics, The University of British Columbia, 1978, 147 pages.

Shawn Kevin Kelly, "A System for Efficient Neural Stimulation with Energy Recovery", Massachusetts Institute of Technology, Oct. 2003, 195 pages.

(Continued)

*Primary Examiner* — Allen Porter, Jr.
(74) *Attorney, Agent, or Firm* — Snell & Wilmer L.L.P.

(57) ABSTRACT

Neural stimulation is effected by a stimulus current pulse. The current pulse is initially of an amplitude to rapidly induce a desired electrode voltage, and is subsequently of reduced amplitude to control electrode voltage in a desired manner. This can effect a reduced peak electrode voltage while delivering a given amount of charge. Optimization of the current pulse may further involve parameterising an electrode current waveform as a sequence of piecewise constant steps, each step having substantially the same duration as all other steps and each step having a calculatable amplitude, and identifying electrode-tissue interface (ETI) parameters. For each step of the pulse, the respective step amplitude is then calculated using the identified ETI parameters to optimise the electrode voltage.

14 Claims, 3 Drawing Sheets

(56) References Cited

OTHER PUBLICATIONS

Mark Halpern., "Optimal Current Waveforms for Neural Stimulation", Medical Bionics Conference Handbook, Sir Mark Oliphant International Frontiers of Science and Technology Conference Series, Lorne, Nov. 12-19, 2008; p. 47.

Mark Halpern., "Optimal Current Waveforms for Neural Stimulation", Abstract of Poster P27 presented at Medical Bionics Conference, Sir Mark Oliphant International Frontiers of Science and Technology Conference Series, Lorne, Nov. 12-19, 2008; 1 page.

* cited by examiner

NEURAL STIMULATION

CROSS-REFERENCE TO RELATED APPLICATION

The present application claims priority from the U.S. Provisional Application No. 61/243,693 filed on Sep. 18, 2009.

TECHNICAL FIELD

The present specification relates to neural stimulation, and in particular concerns a device for neural stimulation, a method for neural stimulation, and a computer program product.

BACKGROUND

Many implanted medical devices rely on electronic circuits to provide electric stimulation of nerves. Such devices include retinal implants and cochlear implants, where the electrical stimulation is used to transfer information to the brain, as well as devices for applications where the stimulation is used for motor control. For chronic use in patients, it is necessary that such devices transfer a zero net charge, and so the use of charge-balanced rectangular biphasic current pulses for neural stimulation is well established. These pulses often comprise a constant current stimulating cathodic phase, followed by a brief interphase gap in which no stimulation is applied, and then a constant current charge-balancing anodic phase.

Various kinds of neural stimulation performance improvement have been sought by varying the waveform of the signal. For instance variations from the basic symmetric rectangular biphasic current pulse have been investigated for their effect on threshold, for selective recruitment of different sized fibres and for increasing charge delivery capacity of electrodes.

Neural stimulation devices further face certain constraints upon the voltage which may appear on the stimulating electrodes. While miniaturization of neural stimulation devices is desirable, integrated circuit (IC) technologies with reduced device (transistor) size tolerate smaller voltages. Thus, devices using progressively smaller feature semiconductor technologies face limits on the maximum supply voltage available to effect the electrical neural stimulation. While smaller feature semiconductor technologies may be adapted to provide larger electrode voltages, this necessitates increased circuit complexity and power consumption to step up the voltage. Another approach is to use semiconductor fabrication technology which allows both high and low voltage transistors on the same die, however, such specialised devices add to the IC fabrication cost.

Another factor affecting electrode voltage is the need to avoid voltages rising above a certain threshold, to prevent the formation of undesirable chemical products in the tissue surrounding the electrode. One approach for limiting peak electrode voltage involves monitoring the electrode voltage and reducing the current when a prescribed voltage limit is approached.

Implanted devices are generally battery powered and thus have a tight power budget. To reduce the power dissipated in neural stimulation circuitry, careful attention has been paid to design of current sources, and a voltage drive waveform designed to approximately match the electrode voltage under constant current drive has also been proposed. Nevertheless the power budget remains a significant factor in neural stimulation.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

In a first aspect there is a device for neural stimulation, the device comprising:
  at least one electrode for delivering a predetermined amount of charge for electrical stimulation to neural tissue;
  a stimulus current generator to generate a stimulus current pulse containing the predetermined amount of charge for delivery by the electrode, wherein the current pulse comprises a successive series of current steps; and, a processor to calculate the amplitude of each current step, or the duration of
  each current step, or both, in order to minimize peak electrode voltage during the current pulse, while delivering the predetermined amount of charge.

In the simplest implementation the duration of all the current steps is the same. In this case the duration may be selected first, and then the amplitude of each step may be calculated to ensure the peaks of the electrode voltage are minimized. Current steps of equal duration may be advantageous due to ready availability of suitable hardware to deliver stepped currents of constant step duration. A circuit model of the electrode-tissue interface may be used, for instance comprising known values of access resistance $R_a$ ohms, double layer capacitance C Farads and Faradaic resistance R ohms, to calculate the current step amplitudes and minimise peak electrode voltage.

The duration of each current step may be the same or different. When they are different the duration of each successive step may be greater than the preceding one. Current steps of differing duration may be advantageous in effecting greater charge transfer while remaining within a given maximum electrode voltage level, or in effecting transfer of a given amount of charge while minimising a peak electrode voltage value.

When the duration of all the current steps is not required to be the same, it should be possible to reduce the voltage peaks compared to those appearing when the duration of each current step is the same.

However, the simultaneous calculation of amplitudes and durations to minimize peak voltage is difficult. One way of determining the amplitudes and durations is to convert the n equal durations to m pre-specified unequal durations where m is less than n. In particular, each of the m pre-specified unequal durations is equal to a different integer multiple of Tin where T is the total duration of all the pulses. Then for each step, it is possible to calculate the current amplitude that results in the minimum peak electrode voltage during the current pulse.

To find the global minimum peak electrode voltage for the current pulse, it would be necessary to repeat the calculation of current amplitude for each step, for every different permutation of pre-specified durations, and then the minimum can be selected.

The step amplitude, or duration, or both, may be optimised in-vivo, rather than using a modelled equivalent circuit of the electrode tissue interface. The approach to in-vivo optimization begins by supplying an initial constant current, while monitoring the increasing electrode voltage. When the voltage reaches a specified level, or alternatively when a given time has passed, the current is switched to a lower value and this is applied until the monitored electrode voltage again reaches the same value as the previous peak. The current is then reduced to a lower value again and the process is repeated until either the desired charge has been delivered or the available time duration has been used up. So it is the actual behaviour of the electrode-tissue interface and the current source and not the predicted behaviour based on a model that is used to set the switching times. Note that the electrode voltage needs to be continuously monitored and its value is used to determine the next switching time.

According to a second aspect, the present invention provides a method for neural stimulation, the method comprising:

generating a stimulus current pulse, comprising a successive series of current steps, to at least one electrode in order to electrically stimulate neural tissue by delivering a predetermined amount of charge, the stimulus current pulse being a stepped current pulse; and calculating the amplitude of each current step, or the duration of each current step, or both, in order minimize peak electrode voltage during the current pulse, while delivering the predetermined amount of charge.

Examples of the invention may involve specifying algorithms to directly identify electrode-tissue interface parameters. In one example, in which the current pulse comprises n current steps of equal duration $T_s$, an excitation current is applied to the tissue for a period of $T_s$, and the voltage across the electrodes is measured at times $T_s, 2.T_s, \ldots n.T_s$. Transfer function coefficients may be estimated from such voltage measurements, from which an optimised amplitude of each current step may be calculated.

Other examples may further comprise, prior to the calculating step, defining an optimum electrode voltage, and specifying preferable ranges for the step duration.

According to a third aspect the present invention provides a computer program product comprising computer program code means to make a computer execute a procedure for neural stimulation, the computer program product comprising:

computer program code means for delivering a stimulus current pulse to at least one electrode in order to electrically stimulate neural tissue by delivering a predetermined amount of charge, the stimulus current pulse being a stepped current pulse comprising a successive series of current steps; wherein the amplitude of each current step is calculated, or the duration of each current step is calculated, or both are calculated, in order minimize peak electrode voltage during the current pulse, while delivering a predetermined charge

BRIEF DESCRIPTION OF THE DRAWINGS

An example of the invention will now be described with reference to the accompanying drawings, in which.

BEST MODE

A Current Waveform comprising Piecewise Constant Segments with Regular Time Intervals between Transitions The example described here relates to the design of electrical current waveforms for the delivery of electric charge from an electronic circuit through a pair of electrodes into neural tissue for the purpose of evoking stimuli. In particular this example takes an analytical approach to designing electrode stimulation current waveforms in such a way as to reduce the maximum voltage between the two electrodes while delivering a given charge in a specified time.

Figure 2:
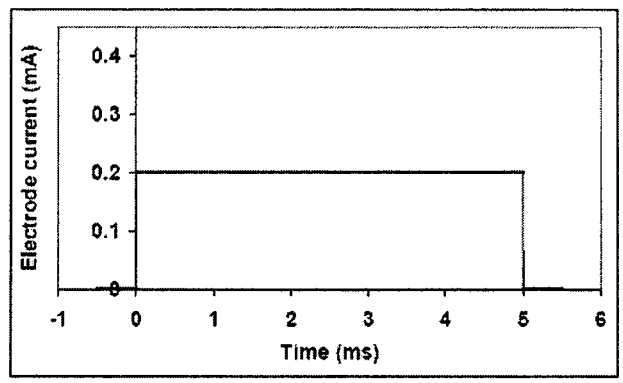
FIG. 2 illustrates a conventional electrode current pulse.

Conventionally, the first phase, also called the stimulation phase, of a biphasic stimulation current waveform has constant amplitude for the total duration of the stimulation phase, as shown in FIG. 2.

Instead, this example provides for piecewise constant (stepped) current waveforms to replace the constant current stimulation phase, wherein the step durations are given and equal, and the step sizes (current amplitudes) are calculated in a manner to minimise the peak voltage between the electrodes, while delivering the required specified amount of electric charge through the tissue.

Reducing the maximum electrode voltage is desirable for several reasons. First, it allows the supply voltage to the current generating electronic circuits to be reduced, thereby reducing power loss in the stimulation circuitry. Second, devices using small feature semiconductor technologies face limits on the allowed size of supply voltage. Third, limiting the maximum electrode voltage can prevent the formation of undesirable chemical products.

Figure 1:
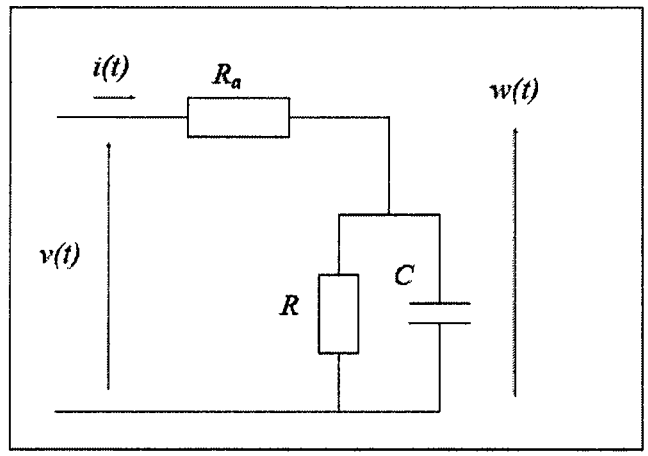
FIG. 1 is a circuit diagram of a model of the electrode-tissue interface.
Figure 4:
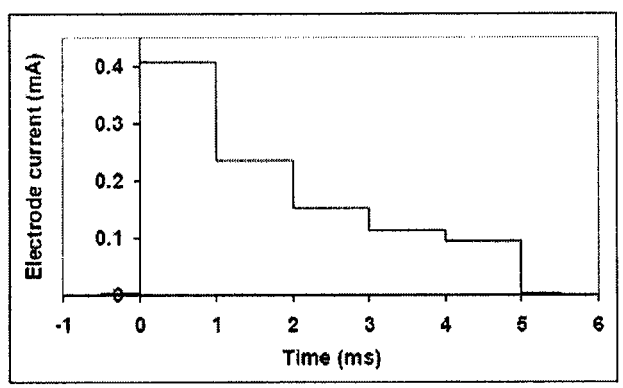
FIG. 4 illustrates an electrode current pulse in accordance with one example of the present invention, consisting of five current steps of decreasing amplitude optimised to maximise delivered charge while minimising electrode voltage.

In this example, optimised stepped current levels are determined from (a) a specification of a stepped electrode current for the stimulation phase, where the steps are of given and equal duration as shown in FIG. 4, and (b) a representation of the electrode-tissue interface by an equivalent linear electric circuit, as set out in FIG. 1. Together, these allow engineering design techniques to be used to determine the optimal amplitudes of the current steps which will both minimise peak electrode voltage and ensure that the required electric charge is delivered.

The basic formulation of the waveform design problem presented here uses an assumed known electric circuit equivalent model of the electrode-tissue interface, as shown in FIG. 1. In a practical in-vitro or in-vivo situation, modifications enabling more direct modelling of the electrode-tissue interface may be used without going through the intermediate step of an equivalent circuit model.

This example is particularly advantageous in that the electrode current design problem can be approached using techniques used for control system design, since zero-order-hold sampled signals are widely used in digital control systems where a digital computer is used to compute signals to drive an analog device in order to achieve desired performance. With the framework used here, the problem of delivering given charge with minimum electrode voltage is closely related to that of designing a current waveform which maximizes charge delivered under the constraint of not exceeding a designated voltage level.

Figure 6:
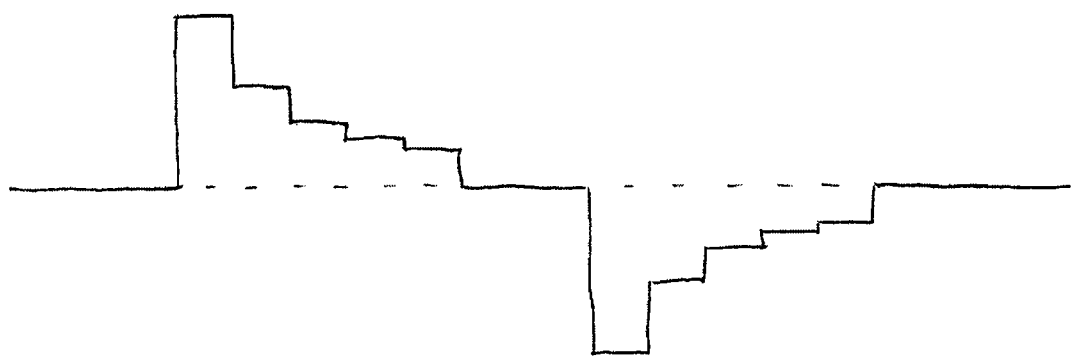
FIG. 6 illustrates a current waveform of a charge balanced biphasic pulse with interphase gap, in accordance with an example of the present invention.

The problem considered in this example is the design of the stimulation current phase, the first part of a biphasic waveform (shown in full in FIG. 6), for the delivery through a pair of electrodes of a specified charge Q coulombs over a specified stimulation phase duration T seconds. For convenience of presentation, the charge is specified positive ie Q>0, while it is known that the stimulation phase is usually negative. The actual negative stimulation phase would be obtained by changing the signs of the currents from the calculated values.

Voltages and currents which are functions of time t are denoted by lower case letters such as v(t). Samples of v(t) taken at time intervals $t=kT_s$ where $k=0, 1, 2, \ldots$ are denoted $v_k$, shorthand for $v(kT_s)$. The z-transform of a sequence $h=\{h_k\}_{k=0}^{\infty}$ is denoted $\hat{h}(z)$ and is given by $$\hat{h}(z) = \sum_{k=0}^{\infty} h_k z^k. \tag{1}$$

With this convention, a stable transfer function has all its poles at values of $z:|z|>1$. Also the symbol z denotes the unit delay.

The electrode-tissue interface is modeled with the circuit of FIG. 1 comprising access resistance $R_a$ ohms, double layer capacitance C Farads and Faradaic resistance R ohms. It is assumed the values of these three parameters are known. With constant electrode current $i(t)=i_0$ applied for $t>0$, the internal voltage w(t) and the electrode voltage v(t), both for $t>0$ are given by $$w(t)=w(0)e^{-t/RC}+i_0R(1-e^{-t/RC}), \tag{2}$$

$$v(t)=w(t)+i_0R_a. \tag{3}$$

Parameterization of stimulation current follows. Firstly, the stimulation phase duration T is broken up into a whole number, n, of discrete time intervals each of duration $T_s$. In alternative examples the stimulation phase duration is broken into intervals of varied duration. Thus in this example $T=nT_s$, where n is a positive integer. Setting n=1 specifies the standard constant current stimulation phase. The current i(t) is parameterized to be piecewise constant over time intervals $T_s$ as follows:

$$i(t) = \begin{cases} 0; & t \le 0, \\ i_k; & kT_s < t \le (k+1)T_s; k = 0, 1, \ldots, n-1, \\ 0; & t > nT_s. \end{cases} \tag{4}$$

The desired charge Q of the stimulation phase is obtained by setting $$\sum_{k=0}^{n-1} i_k = \frac{Q}{T_s}. \tag{5}$$

From (4), i(t) takes on n values $i_k$, which are constrained to satisfy (5). If the current has the form (4), then over each time interval given by $kTs<t\le(k+1)T_s$ where $k=0, 1, \ldots, n-1$, voltage w(t) is given by $$w(t)=w(kTs)e^{-(t-kTs)/RC}+i_kR(1-e^{-(t-kTs)/RC}) \tag{6}$$

and v(t) is given by $$v(t)=w(t)+i_kR_a. \tag{7}$$

This example takes a linear programming approach to minimizing peak electrode voltage, as follows. From (2) and (3), the maximum value of v(t) in response to a current step occurs either at the beginning or the end of that current step. Thus the problem of minimizing the peak electrode voltage in response to a current of the form (4) requires consideration of v(t) only at sample times $t=kT_s$. This allows the electrode-tissue dynamics to be represented by discrete-time versions of (2) and (3) namely $$w_k=\alpha w_{k-1}+i_{k-1}R(1-\alpha), \tag{8}$$

$$v_k=w_k+i_{k-1}R_a \tag{9}$$

where $k=1, 2, \ldots, n$ and $$\alpha=e^{-T_s/RC}. \tag{10}$$

Denoting the minimum peak value of v(t) by J, the problem of calculating J can be formulated as the following finite linear program where K is a variable introduced to bound $v_k$.

$$J = \min_{i_k, w_k, v_k} \gamma \tag{11}$$

subject to $$i_k \ge 0; k = 0, 1, \ldots, n-1, \tag{12}$$

$$\sum_{k=0}^{n-1} i_k = \frac{Q}{T_s}, \tag{13}$$

$$w_0 = 0, \tag{14}$$

$$w_k = \alpha w_{k-1} + i_{k-1} R(1 - \alpha); k = 1, 2, \ldots, n, \tag{15}$$

$$v_k = w_k + i_{k-1} R_a; k = 1, 2, \ldots, n, \tag{16}$$

$$v_k \le \gamma; k = 1, 2, \ldots, n. \tag{17}$$

This optimization problem can be solved numerically to determine the current step sizes and the minimized peak electrode voltage. The voltages w(t) and v(t) between the sample values can be calculated from (6) and (7). There is scope to modify the problem by the addition of further inequality or equality constraints on variables $i_k, v_k, w_k$. For example bounds could be placed on the values of some of the $i_k$ or on their rate of change.

It is noted that, in an alternative approach to obtaining the solution to the problem (11)-(17). direct calculation of stimulation current may occur. This alternative approach occurs without solving a numerical optimization. It can be shown that the solution to the optimization problem (11)-(17) has the property that the electrode voltage satisfies $v_1=v_2=\ldots=v_n>0$. This enables the values of $i_0, \ldots, i_{n-1}$ and $v_1, \ldots, v_n$ to be constructed directly. The procedure involves three steps.

Firstly, the discrete-time transfer function $\hat{h}(z)$ of the electrode-tissue equivalent circuit voltage response at times $t=kT_s$ to a unit step current applied over one sample time $0<t\leq T_s$ is determined. Then the relation between the electrode voltage samples and the current values is given by $$\hat{v}(z)=\hat{h}(z)\hat{i}(z). \tag{18}$$

Eliminating $w_k$ from (8) and (9) gives $$\hat{h}(z) = \frac{b_1 z + b_2 z^2}{1 - \alpha z} \tag{19}$$

where $$b_1 = R_a + R(1-\alpha), \tag{20}$$

$$b_2 = -\alpha R_a. \tag{21}$$

Secondly, a stepped electrode current denoted $\hat{f}(z)$ with the form of (4) which would give an electrode voltage satisfying $$v_0=0, v_k=1; k=1,2, \tag{22}$$

or equivalently $$\hat{v}(z) = \frac{z}{(1-z)} \tag{23}$$

is calculated. Now $\hat{f}(z)$ such that $$\hat{v}(z) = \hat{f}(z)\hat{h}(z) = \frac{z}{(1-z)} \tag{24}$$

is given by $$\hat{f}(z) = \frac{1}{(1-z)}\frac{z}{\hat{h}(z)} \tag{25}$$

$$= \frac{1}{(1-z)}\frac{1/b_1(1-\alpha z)}{(1+(b_2/b_1)z)} \tag{26}$$

Thirdly $\hat{f}(z)$ is truncated to n terms and then scaled to give a current $\hat{i}(z)$ which satisfies the charge constraint (5):

$$\hat{i}(z) = \frac{Q}{T_s}\frac{\sum_{j=0}^{n-1} f_j z^j}{\sum_{j=0}^{n-1} f_j}. \tag{27}$$

Moreover the value of $v_1, v_2, \ldots, v_n$ is given by the scaling factor above, so that $$J = \frac{Q}{T_s}\frac{1}{\sum_{j=0}^{n-1} f_j}. \tag{28}$$

This approach can be used to calculate numerical solutions, identical to those from (11)-(17). Furthermore a closed-form solution for the minimum value of the peak electrode voltage can be obtained by resolving (26) into two partial fractions, followed by truncating the individual series expansions and scaling to obtain:

$$J = \frac{Q}{T_s}\frac{(R_a+R)^2(1-\alpha)}{(R_a+R)(1-\alpha)n + R_a\left(1-\left(\frac{R_a\alpha}{R_a+R(1-\alpha)}\right)^n\right)}. \tag{29}$$

The above can even give more general results. Suppose the solution to (11)-(17) for given parameters and charge $Q_0$ has a minimum peak electrode voltage of value $J(Q_0)$. Then the following hold:

1) Scaling with charge: If only the charge is changed to $Q=cQ_0$ where $c>0$, the solution to (11)-(17) becomes $$J(cQ_0)=cJ(Q_0); c>0, \tag{30}$$

2) Maximizing charge with given bound on electrode voltage: Given $\beta>0$ $$\max_{v_k \leq \beta} Q = \frac{Q_0}{J(Q_0)}\beta \tag{31}$$

Example 1

Figure 3:
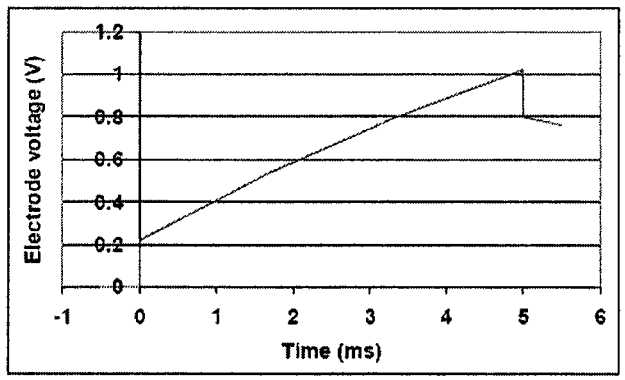
FIG. 3 illustrates the voltage profile arising on the stimulating electrodes when the conventional current pulse of FIG. 2 is delivered to tissue.

This example uses electrode-tissue interface parameter values $R_a=1100\Omega$, $C=0.98\,\mu F$, $R=10\,k\Omega$, with charge parameters $Q=1\,\mu C$, $T=5$ ms. A constant-current stimulation phase is obtained by setting n=1. For this case, there is no scope for optimization. The electrode voltage is obtained by evaluating (6) and (7) with initial condition w(0)=0 and current $i_0$ given by (5). Plots are shown in FIGS. 2 and 3.

Figure 5:
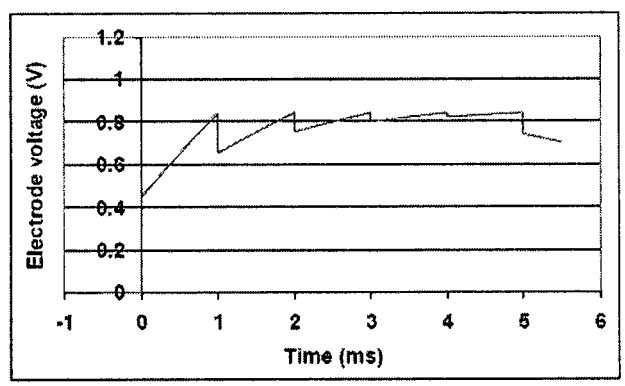
FIG. 5 illustrates the voltage profile arising on the stimulating electrodes when the current pulse of FIG. 4 is delivered to tissue.

To illustrate the approach shown in this paper, a five-step current waveform is obtained by setting $T_s=1$ ms and n=5. Solving (11)-(17) gives the sampled voltages $w_k$ and $v_k$ and the currents $i_k$. The voltage values between time samples are obtained from (6) and (7). Electrode current and voltage plots are in FIGS. 4 and 5.

Results for various values of n and $T_s$ chosen to keep the stimulation phase duration $T=nT_s$ constant at 5 ms are shown in Table I, obtained using (29). For this example, the maximum electrode voltage can be reduced by approximately 21% through the use of this approach. Most of the performance improvement is achieved with 5-10 steps.

TABLE I

Values of minimized peak electrode voltage for a 5 ms stimulation phase.

| n | $T_s$ (ms) | J (volts) | Voltage reduction (%) |
|---|---|---|---|
| 1 | 5 | 1.019 | 0 |
| 2 | 2.5 | 0.906 | 11 |
| 5 | 1 | 0.843 | 17 |
| 10 | 0.1 | 0.823 | 19 |
| 100 | 0.05 | 0.807 | 21 |
| 1000 | 0.005 | 0.806 | 21 |

This example thus provides for a neural stimulation current design approach using a current waveform comprising piecewise constant segments with regular time intervals between transitions, in place of the often used single constant current. The use of numerical optimization using a finite linear program to compute the current step sizes to minimize peak electrode voltage has been demonstrated. A direct approach for synthesizing the optimal current steps is also given. Table I shows that this approach gives current waveforms which can deliver a given charge to a specified load with useful voltage headroom reduction below that required with conventional rectangular current pulses. This technique thus attempts to directly control the electrode voltage. The approach presented here has the advantage of reducing the peak electrode voltage.

Figure 7:
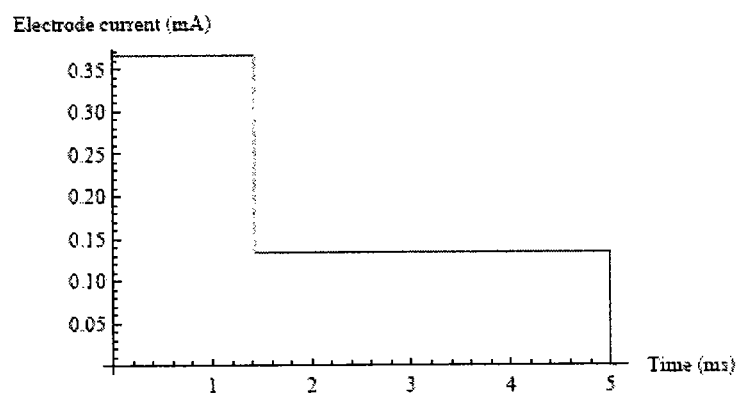
FIG. 7 illustrates an electrode current pulse in accordance with another example of the present invention, consisting of two current steps of differing duration and amplitude, each step amplitude being optimised to minimise electrode voltage for a given charge transfer.
Figure 8:
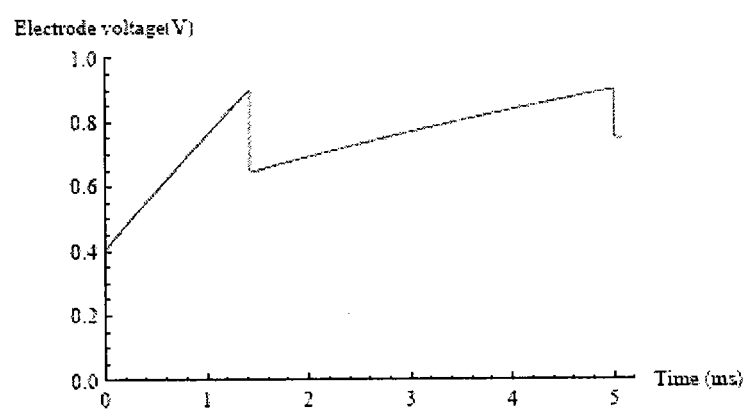
FIG. 8 illustrates the voltage profile arising on the stimulating electrodes when the current pulse of FIG. 7 is delivered to tissue.

A Current Waveform Comprising Piecewise Constant Segments with Non-Constant Time Intervals between Transitions It is to be noted that in alternative examples each current step may be of a duration which differs from the duration of one or more other steps of the current pulse. One such alternative example is shown in FIGS. 7 and 8. FIG. 7 illustrates an electrode current pulse in accordance with another examples of the present invention, consisting of two current steps of differing duration and amplitude, optimised to minimise electrode voltage for a given charge transfer. FIG. 8 illustrates the voltage profile arising on the stimulating electrodes when the current pulse of FIG. 7 is delivered to tissue. It will be appreciated that in alternative examples the current pulse may comprise more than two steps, each of differing duration to the other steps.

There follows details of two examples of the minimization of peak voltage when delivering a given charge Q in a given total duration T, which is divided up into m possibly unequal time durations, denoted $d_1, d_2, \ldots, d_m$, where $d_1$ will be the smallest if the current amplitudes are continuously variable but not if they are discrete. Recall that when the durations are equal, total charge delivery duration T is divided into n equal subintervals, each of duration T/n. The approach described here for calculating current amplitudes for unequal pulse durations is to specify each pulse duration $d_i$ to be an integer multiple of T/n so that $d_i = K_i T/n$; $i=1, 2, \ldots, m$ with each $K_i$ being a positive integer with all $K_i$ jointly satisfying:

$$K_1 + K_2 + \ldots + K_m = n \tag{32}$$

and require that the current amplitudes be set constant within each entire subinterval $d_i$. For example FIG. 7 is obtained using n=14, m=2, with $K_1=4$ and $K_2=10$. That is to say there are two pulses of unequal duration; the first is 2/7 of the total duration, the second is 5/7 of the total.

Linear Programming

The incorporation of unequal pulse durations according to the approach outlined above can be achieved by modifying the linear programming example in equations 11 to 17 through the addition of constraints enforcing equal currents during each subinterval. These m additional constraints are $$i\_\{0\} = i\_\{1\} = \ldots = i\_\{K_1 - 1\} \tag{33}$$

$$i\_\{K_1\} = i\_\{K_1 + 1\} = \ldots = i\_\{K_1 + K_2 - 1\} \tag{34}$$

$$\vdots$$

$$i\_\{K_1 + K_2 + \ldots + K_{m-1}\} = \tag{35}$$
$$i\_\{K_1 + K_2 + \ldots + K_{m-1} + 1\} = \cdot \ldots = i\_\{K_1 + K_2 + \ldots + K_m - 1\}$$

(note that A_B represents a subscript $A_B$)

An in-vivo Example

It is further noted that step amplitude and/or duration may be optimised in vivo, rather than relying upon a modelled equivalent circuit of the electrode-tissue interface. Provided below is a discussion of one example for determining optimised current step amplitudes in an example comprising n current steps of equal duration. This algorithm is for identifying the electrode tissue interface (ETI) transfer function coefficients and shows how they are used to determine the optimal current waveform.

The problem is first defined. The charge to be delivered is Q coulombs. Let n be the number of steps in the stimulation phase. The total stimulation phase duration is seconds. The duration of each step is then $T_s = T/n$ seconds. Define a reference current $I_{ref}$ given by $$I_{ref} = Q/T. \tag{101}$$

The aim is to determine the current i(t) which is parameterized to be piecewise constant over time intervals $T_s$ as follows:

$$i(t) = \begin{cases} 0; & t \leq 0, \\ i_k; & kT_s < t \leq (k+1)T_s; k = 0, 1, \ldots, n-1, \\ 0; & t > nT_s, \end{cases} \tag{102}$$

and also the minimised peak voltage which is the value of $v(T_s), v(2T_s), \ldots v(nT_s)$ when these are made equal to each other. The currents calculated should satisfy:

$$\sum_{k=0}^{n-1} i_k = \frac{Q}{T_s}, \tag{103}$$

and the measured values of $v(T_s), v(2T_s), \ldots v(nT_s)$ should be equal to each other.

The next step is identification of ETI transfer function coefficients. The electrode-tissue interface transfer function coefficients to be identified are $h_i, h_2, \ldots, h_n$. The excitation current i(t) is $$i(t) = \begin{cases} 0; & t \leq 0, \\ I_{ref}; & 0 < t \leq T_s; \\ 0; & t > T_s. \end{cases} \tag{104}$$

Apply this excitation current to the electrodes. Measure the voltages $v(T_s), v(2T_s), \ldots, v(nT_s)$. Then the estimated transfer function coefficients are $$h_k = \frac{v(kT_s)}{I_{ref}}; k = 1, 2, \ldots, n. \tag{105}$$

For the scheme to work, the voltage response should be monotonic decreasing and positive for $t > T_s$.

It is then possible to calculate optimal current levels, by solving the following triangular linear system of n equations in n unknowns:

$$1 = x_0 h_1 \tag{106}$$

$$1 = x_0 h_2 + x_1 h_1 \tag{107}$$

$$1 = x_0 h_3 + x_1 h_2 + x_2 h_1 \tag{108}$$

$$\ldots$$

$$\ldots$$

$$1 = x_0 h_n + x_1 h_{n-1} + \ldots + x_{n-1} h_1. \tag{109}$$

Solving these from the top, $x_0=1/h_1>0$, $x_1=1/h_1(1-x_0h_2)>0$, $x_2=1/h_1(1-x_0h_3-x_1h_2)>0$. Continuing till $$x_{n-1} = 1 \bigg/ h_1\left(1 - \sum_{i=0}^{n-2} x_i h_{n-i}\right) > 0$$

gives all $x_i$.

Calculate $$\beta = \sum_{i=0}^{n-1} x_i.$$

The optimal currents are then $$i_k = x_k \frac{Q}{T_s \beta}; k = 0, 1, \ldots, n-1, \quad (110)$$

and the predicted minimised peak voltage is $$v_k = \frac{Q}{T_s \beta}; k = 1, 2, \ldots, n. \quad (111)$$

A numerical example of implementation of this in vivo optimisation technique follows. With n=3, Q=40 nC, T=400 μs, then $T_s$=133 μs. Then $I_{ref}$=Q/T=100 uA. The excitation current is:

$$i(t) = \begin{cases} 0; & t \leq 0, \\ 100 \text{ μA}; & 0 < t \leq 133 \text{ μs}; \\ 0; & t > 133 \text{ μs}. \end{cases} \quad (112)$$

The measured voltage response was $v_1$=0.121V, $v_2$=0.042V, $v_3$=0.035V. Then the optimal stimulation current waveform is $i_0$=140.383 μA, $i_1$=91.6549 μA, $i_2$=67.9622 μA. The predicted value of $v_1$, $v_2$, $v_3$ is v=0.169863V.

The in-vivo example can also be modified to allow for Non-Constant Time Intervals between Transitions modifying the system of equations (106) to (109). This involves setting certain of the xi equal to each other and also removing one equation for each pairing up of xi. For example if it is desired that x1=x2, then eqn (107) should be removed since we do not want to have a voltage peak due to current x1. In this way, the set of equations n equations (106) to (109) in n unknowns becomes a set of m equations in m unknowns.

Building a Stepped Current Waveform in Real-Time

We now describe how to build a stepped current waveform in realtime without using a model of the electrode-tissue impedance. The approach minimises the peak voltage in the sense that it ensures the voltage at the end of each current step, (except for the last one) is equal. This is what our previous approach tries to do for all the steps (including the last one) using a model. The approach begins by supplying an initial constant current, while monitoring the increasing electrode voltage. When the voltage reaches a specified level, or alternatively when a given time has passed, the current is switched to a lower value and this is applied until the monitored electrode voltage again reaches the same value as the previous peak. The current is then reduced to a lower value again and the process is repeated until either the desired charge has been delivered or the available time duration has been used up. So it is the actual behaviour of the electrode-tissue interface and the current source and not the predicted behaviour based on a model that is used to set the switching times. Note that the electrode voltage needs to be continuously monitored and its value is used to determine the next switching time.

This method allows a quantised current to be used. It does not allow a given charge to be delivered in a given duration in a "single shot procedure". For example, if we stop after the pre-specified duration has elapsed and the charge is insufficient by a factor of say 20%, then the waveform should be recalculated with amplitudes 20% bigger.

In contrast, the previous stepped current approach involves pre-specifying total charge and total duration and the number of current steps. If the model used to calculate the current amplitudes is poor, the required charge is still delivered in the specified duration, but the voltage minimisation may be degraded and would be evident by the voltage peaks at the end of each current pulse not being equal to each other.

In contrast to that, the approach presented here proceeds by making the voltages equal, except for the last one if the procedure stops at prespecified charge or duration. The signal may need to be tuned by changing some of the initial current, peak voltage and duration of the initial pulse. A modification to the approach can be made to allow the construction of fixed-pulse-width variable-amplitude current signals. Other methods of designing these have recently been proposed, and demonstrated using 2 and 5 steps. The concept here does not depend on the assumed linear behaviour of the electrode-tissue interface and in addition is less affected by rate limitations at the current source output. This should allow better performance to be obtained giving more reduction of peak voltage with a given number of steps. It should also make feasible the use of a larger number of steps to give further reductions in voltage. However it does not give both the demanded charge and the demanded total duration without modification.

It will be appreciated by persons skilled in the art that numerous variations and/or modifications may be made to the invention as shown in the specific examples without departing from the spirit or scope of the invention as broadly described. The present examples are, therefore, to be considered in all respects as illustrative and not restrictive.

The invention claimed is:

1. A device for neural stimulation, the device comprising:
at least one electrode for delivering a predetermined amount of charge for electrical stimulation to neural tissue;
a stimulus current generator to generate a stimulus current pulse containing the predetermined amount of charge for delivery by the electrode, wherein the current pulse comprises a successive series of current steps; and
a processor to calculate the amplitude of each current step, or the duration of each current step, or both, such that the electrode voltage reaches the same peak electrode voltage at the end of two or more of the successive series of current steps, in order to minimize peak electrode voltage during the current pulse, while delivering the predetermined amount of charge.

2. A device according to claim 1, wherein the duration of all the current steps is the same.

3. A device according to claim 1, wherein the duration of each current step is different.

4. A device according to claim 3, wherein the duration of each successive step is greater than the preceding one.

5. A method for operating a neural stimulations device, comprising:
- generating a stimulus current pulse, comprising a successive series of current steps, to at least one electrode in order to electrically stimulate neural tissue by delivering a predetermined amount of charge, the stimulus current pulse being a stepped current pulse; and
- calculating the amplitude of each current step, or duration of each current step, or both amplitude and duration, such that the electrode voltage reaches the same peak electrode voltage at the end of two or more of the successive series of current steps, in order minimize peak electrode voltage during the current pulse, while delivering the predetermined amount of charge.

6. A method according to claim 5, wherein all the current steps have equal duration and the length of the duration is selected first, and then the amplitude of each step is calculated to minimize the peak electrode voltage.

7. A method according to claim 6 wherein a circuit model of the electrode-tissue interface is used to calculate the current step amplitudes and minimize peak electrode voltage.

8. A method according to claim 7 wherein the circuit model comprises known values of access resistance $R_a$ ohms, double layer capacitance C Farads and Faradaic resistance R ohms, to calculate the current step amplitudes to minimize the peak electrode voltage.

9. A method according to claim 5 wherein all the current steps do not have equal duration, and the durations are calculated as follows:
- converting n steps having equal duration to m steps having pre-specified unequal durations where m is less than n, and wherein each pre-specified duration is equal to a different integer multiple of T/n, where T is the total duration of all the pulses; then given these durations, calculating the amplitude of each step that minimizes the peak electrode voltage.

10. A method according to claim 9, comprising the further step of finding the global minimum peak electrode voltage for the current pulse, by repeating the calculation of current amplitude for each step, for every different permutation of pre-specified durations, and then selecting the minimum.

11. A method according to claim 5, wherein the step duration is optimised in-vivo, by:
- supplying an initial constant current and monitoring the increasing electrode voltage;
- then, switching the current to a lower value and applying the lower value of current until the monitored electrode voltage again reaches the same value as it had at the previous switching event;
- and then switching the current to an even lower level; and
- repeating this process until the desired amount of charge has been delivered.

12. A method according to claim 5, comprising the further step of specifying algorithms to directly identify electrode-tissue interface parameters.

13. A method according to claim 12 wherein the current pulse comprises n current steps of equal duration $T_s$, an excitation current is applied to the tissue for a period of $T_s$, and the voltage across the electrodes is measured at times $T_s$, $2.T_s$, ... $n.T_s$, so that transfer function coefficients are estimated from the voltage measurements, from which an optimized amplitude of each current step is calculated.

14. A method according to claim 12, wherein prior to the calculating step, an optimum electrode voltage is defined, and ranges for the step duration are specified.

* * * * *